(12) United States Patent
Eul

(10) Patent No.: US 12,105,501 B1
(45) Date of Patent: Oct. 1, 2024

(54) ORGAN MODEL PRODUCTION SYSTEM

(71) Applicant: Alexander Paul Eul, Camarillo, CA (US)

(72) Inventor: Alexander Paul Eul, Camarillo, CA (US)

(*) Notice: Subject to any disclaimer, the term of this patent is extended or adjusted under 35 U.S.C. 154(b) by 0 days.

(21) Appl. No.: 18/471,285

(22) Filed: Sep. 20, 2023

(51) Int. Cl.
G05B 19/4099 (2006.01)
G06T 15/08 (2011.01)
G16H 10/60 (2018.01)

(52) U.S. Cl.
CPC .......... *G05B 19/4099* (2013.01); *G06T 15/08* (2013.01); *G16H 10/60* (2018.01); *G05B 2219/49023* (2013.01); *G06T 2210/41* (2013.01)

(58) Field of Classification Search
CPC ...... G05B 19/4099; G05B 2219/49023; G06T 15/08; G06T 2210/41; G16H 10/60
USPC .................................... 700/98, 118; 382/131
See application file for complete search history.

(56) References Cited

U.S. PATENT DOCUMENTS 9,968,257 B1 * 5/2018 Burt .................... A61B 5/0035
2018/0144219 A1 * 5/2018 Kalisman ............... B33Y 50/00
2023/0225698 A1 * 7/2023 Pernot .................. A61B 8/4416
600/407

FOREIGN PATENT DOCUMENTS

CN 113920213 A * 1/2022 ......... G01R 33/4835

* cited by examiner

*Primary Examiner* — Chun Cao
*Assistant Examiner* — Michael Tang
(74) *Attorney, Agent, or Firm* — Robert R. Lerma

(57) ABSTRACT

The methods, process, and apparatus of the present invention produces a structurally representative organ model using magnetic resonance imaging scan information of a organ and a patient's medical history and physiology. This is accomplished by mathematically convolving the scan information with a second order ranked tensor matrix encoded with the patient's physiological information as it relates to the scanned organ and their medical profile. The convolved scan information and encoded matrix are computer processed to produce a 3D printer driver file which is used to print a structurally representative organ model conforming to the patient's physiology.

9 Claims, 3 Drawing Sheets

ORGAN MODEL PRODUCTION SYSTEM

BACKGROUND OF THE INVENTION

The field of the invention is biological organ replication in a non-biological medium, also known as organ model production. Replicating a complex organ while the organ model maintains the properties of the tissue as the tissue characteristics vary in cross section while also maintaining the complex structure of the external and internal features of the original organ is accomplished with the present invention. Producing an organ model with the look and feel of the original organ provides medical professionals with an opportunity to practice surgical skills in an improved training environment. Currently, organ models are created in a manner which does not retain the look and feel of a real organ because they do not reproduce the nuances of tissue variousness throughout an organ nor reproduce complex internal and external features driven by cellular structure. Described is a novel process and a system to produce an organ model providing the nuances of tissue variousness and complex internal and external features present in the original biological organ. The source dataset, which is uniquely processed as described herein, is derived from readily available magnetic resonance imaging techniques. The end device which produces the replicated organ is an additive layer printer driven by software instructions generated by the unique software process of the present invention. The present invention combines software processing, system hardware, and network connectivity to produce an organ model, having the mechanical and the structural features of the originally scanned biological organ, for use as a novel solution to improve surgical and diagnostic training for highly skilled medical professionals and students.

BRIEF SUMMARY OF THE INVENTION

The present invention provides hospital staff, medical school students, medical school residents, or other persons, the means to practice or refine interventional radiology surgical skills, surgical motor skills, surgical planning, surgical coordination among the various medical fields, cardiovascular interventional radiology, and neurological interventional radiology, by providing an additive layer printed cardiovascular model specific to a particular patient's physiology. The cardiovascular model maintains mechanical accuracy and cardiovascular spatial accuracy by mathematically convolving the magnetic resonance imaging (MRI) information of the scanned organ with a second order ranked tensor matrix encoded with the patient's physiological information as it relates to the scanned organ and their medical profile. In a magnetic resonance system, one or more components that manipulate, enhance or otherwise manipulate image data is an image processor. Encoding the second order ranked tensor with the patient's physiological data, the organ's cellular structure, patient age, patient health, and the patient's race is novel and is not in practice in the field of producing organ models. The result of convolving the MRI information with the encoded matrix is a dyadic product. The dyadic product is further computer processed, in a number of steps, resulting in a driver file suitable for execution on an additive layering printer using a thermoplastic filament. The system by which the organ model is produced includes a number of computer systems, large amounts of computer memory, a network to establish electrical communication amongst the computer systems as well as the additive layering printer. Though the invention described herein specifically describes a cardiovascular organ the invention may be used to produce a model of any body part, of any biological species, which may be scanned using MRI technology.

BRIEF DESCRIPTION OF THE DRAWINGS

The features described above, other features, aspects, and advantages of the present invention will become better understood with regard to the following description, appended claims, and accompanying drawings where:

DETAILED DESCRIPTION OF THE INVENTION

Figure 1:
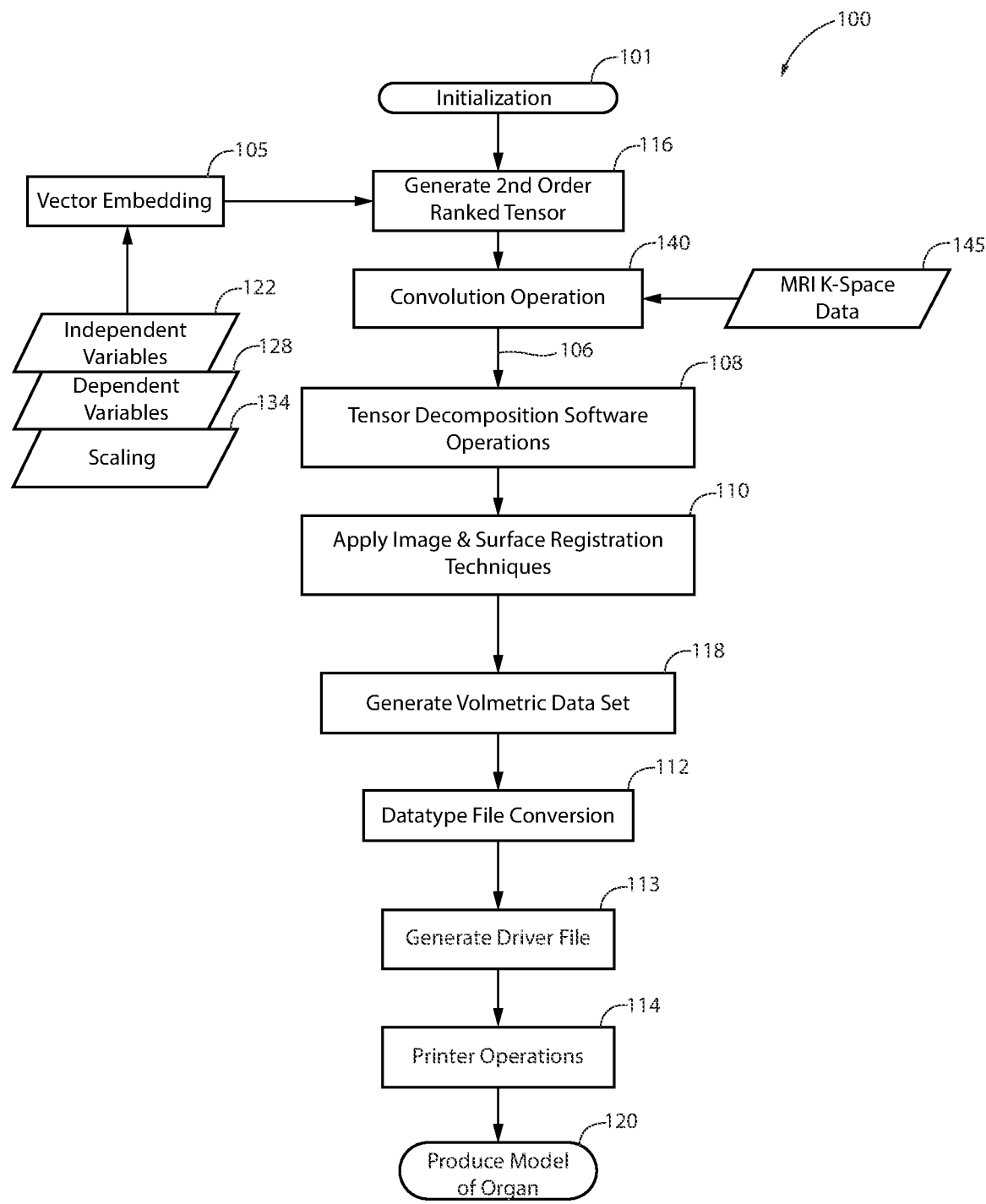
FIG. 1 is a drawing depicting the major process steps and their preferred order of execution in order to practice the present invention.

The present invention provides hospital staff, medical school students, medical school residents, or other persons, the ability to produce a 3-D cardiovascular model which is both cardiovascular-mechanically accurate and cardiovascular-spatially accurate relative to an MRI scan of a patient's heart. The MRI, as a course of normal operation, produces scan information in the form of k-space data 145 set, where k-space data 145 set is an array of numerical values representing spatial frequencies corresponding to the physical characteristics of the cardiovascular organ being scanned. This cardiovascular model accuracy is attributed to the process of performing a mathematical convolution 140 of a nine-term, second order rank tensor 116 a K Space data 145 set forming a dyadic product 106. The dependent variables 128 of the nine-element, second order ranked tensor 116 are elasticity, plasticity, and fracture. The independent variables 122 of the nine-term, second order rank tensor 116 contain cellular composition information such as fibroblast cells, epithelial cells, and endothelial cells, where the fibroblast cells, epithelial cells, and endothelial cells optimize the organ's representation for both mechanical property space and the spatial property space in the resultant 3-D organ model 120. Each of the independent variables 122 within the nine-term, second order ranked tensor 116 is scaled by the tensor's rank, where the scaling 134 represents the patient's age, patient's race, and state of health in the resultant 3-D model. The values used for scaling 134 the nine-term, second order ranked tensor 116 are encoded by patient health quantifiable factors, communicated on bite stream 226, which are defined as patient age, race and state of health submitted to a vector embedding database 105 as a patient history form. The vector embedding database 105 is used to encode the digital logic of the nine-term, second order ranked tensor 116 where the preferred embodiment uses Pinecone implemented by the Python programming language. The vector database program performs "vector embeddings" onto the vector database's input, which is the patient history form. In other words, vector databases and vector embeddings 106 work together, and are distinct from one another.

Specifically, vector embeddings 106 are a collection of words from a given input (i.e. the patient history form) in which these words are converted into arrays of numbers (i.e. vectors), whereby these arrays contain patterns of relationships. The combinatorics of these given arrays comprise a multi-dimensional vector projection as a means to measure similarity. Where the idea of similarity in this context is the projecting of the information found within the given patient history form and mapping those data points to a scaling of those data points, in which such a scaling is parameterized against patient age and patient ethnicity. Once the vector embeddings 106 are created, these embeddings may be stored in a database.

The dyadic product 106 serves as the input of the tensor decomposition software operations 108. The tensor decomposition software 108 is hosted on software processing platforms, the preferred embodiment uses AlphaTensor to perform tensor decomposition, which initializes 101 on a Client computer 340. A description of Tensor Decomposition software operations 108 is a simple and general framework for extracting correlations and low-dimensional structure from tensor-embedded datasets. The preferred embodiment uses Non-Negative Matrix Factorization to implement Dimensionality Reduction in Tensor Decomposition software operations 108. The software operations 108 is available as on off the shelf product known as Alpha Tensor.

The output of the convolution operation is time-acquisition optimized by tensor decomposition software operations 108. Time-acquisition optimization is defined by the initialization of a dimensionality reduction of time complexity which occurs at the time the patient health quantifiable factors are inputted into the vector embedding database 105, which is communicated on bite stream 288, this dimensionality reduction minimizes the time complexity of the invention's process as a means to produce the 3-D printed model faster than current methods and processes.

Dimensionality Reduction is invoked to extract simple structure from large-scale datasets. The techniques of Dimensionality Reduction re-orders the rows and columns of large-scale datasets (i.e. high-dimensional matrices such as the K-space data set 145) to reveal their underlying structure. This is to say, Dimensionality Reduction performed by tensor decomposition "prunes-out" elements of a large-scale dataset which do not contribute to the function of the structure. Non-Negative Matrix Factorization is a technique to implement the necessary Dimensionality Reduction.

The benefits of Non-Negative Matrix Factorization are sparse representation of the embedded-data (i.e. the data within the matrix which is used to generate the structure of the printed organ model is minimized within the dataset which speeds up organ production). Recombination of the voxels within the cells of the dataset being subjected to Non-Negative Matrix Factorization requires a summation of those discrete voxels within the dataset while avoiding shearing of those discrete voxels within the dataset to reconstruct the whole organ structure. Shearing is present when voxels on one plane of both a feature space and a function space remain unchanged while all other voxels of both the feature space and function space are shifted parallel to that plane. A feature space is the space containing all possible anatomic components of a 3-D printed organ model, and a function space is the space containing all possible physiologic components of a 3-D printed organ model; and discrete voxels can be embedded with whole anatomical features and do not require multiple voxels within the matrix to represent a specific feature of a given organ. The anatomical features are those features contained in the vector embedding 105.

The Host Computer 330 collects the K-space dataset 145 via the MRI console interface 332. The Client computer 340 performs a phase encoding step where element k in the space of encoding steps P is obtained from the MRI console interface 332. For each key/of an arbitrary element k where:
 $l \in \{elasticity, plasticity, fracture\}$
is associated with the paired key m where:
 $m \in \{x, y, z\}$
The Client Computer 340 then interprets the given patient history obtained from the patient history form 134 which is used as input to the supervised learning gradient methods also using respective values of the paired key m, as defined above. The Client Computer 340 projects this embedded data onto the feature space given by:
 $l \in \{elasticity, plasticity, fracture\}$
and then interpolates the embedded data onto the function space given by:
 $P \in \{k_1, \ldots, k_n\}$
The result of convolving 140 the vector embedded second ranked tensor 116 with K-space dataset 145 results in a transformation 106 leading to an interpreted voxel volume 118 representing the mechanical, structural, and cellular composition of the originally scanned organ.

A classification of the problem concerning large-scale datasets that do not undergo Dimensionality Reduction is identified as a Co-Clustering, a problem which should be avoided.

The described process of generating the 3-D organ model retains greater structural representation, in comparison to currently produced methods and processes, due to the use of fibroblast cells, epithelial cells, and endothelial cells as the independent variables 122 in the nine-term, second order ranked tensor 116; elasticity, plasticity, and fracture for the dependent variables 128 in the nine-term, second order ranked tensor 116; patient age, and patient ethnicity for the rank in the nine-term, second order ranked tensor 116. The dimensionality reduction is defined as the process of transforming data from an initial dimensional space and then reducing this data to a lower dimensional space. The vector embedded nine-term, second order ranked tensor 116 which is an input to the convolution operation 140 captures the deformation of continuous mediums wherein the deformation of continuous mediums is the voxel value parameterization to conserve the mass of a patient's heart that is being printed on a 3-D printer hotbed plate; deformation of continuous mediums is to perform structural transformations of an object (i.e., 3-D models) using mediums (i.e., filaments), in which these mediums, when being used in lieu of the structural transformation, conserves the mass of the object, where such continuous mediums are transformed into physically continuous 3-D printed models using continuous 3-D printer filaments 230, such as continuous polymer-based filaments, continuous metallic-based filaments, or continuous organic-materials-based filaments (identified on bite stream 232) of the 3-D printer 114. The output of the tensor decomposition software operations 108, serves as an input for image and surface registration techniques 110, where the registration techniques are processed using Gradient Estimation Volume Rendering, which may be performed by parallel processing hardware 346 such as a NVIDIA GPU under network control 287. Supervising learning gradients is a powerful technique used to achieve high accuracy in implementing the image and surface processing tasks. Gradient information is used to detect features in images, such as edges, corners, and blobs related to the original organ.

Gradient information can be used to analyze the texture of an image, such as its smoothness, coarseness, and homogeneity related to the original organ. Another image and surface registration technique uses transformation manifolds. A transformation manifold is used to perform surface reconstruction using a set of images or surfaces that are related to each other by a smooth transformation; a smooth transformation is a geometric summation of each computational output of a transformation matrix and a phase encoding step of k-space, for all phase encoding steps within the k-space. This means that the images or surfaces can be smoothly deformed into each other without any sharp discontinuities as part of the processing to produce the organ model. Merging resources is used as one image and surface registration technique and results in merging multiple sets of points or measurements of a surface can create a more accurate and complete 3D model of the organ model's surface.

Once the image and registration techniques have been applied 110 a volumetric data set is then compiled 118 which is then subjected to a compatible datatype file conversion 112. The data file type conversion 112 results in a 3-D printer compatible driver file 113 such as an STL formatted file which is network communicated on line 218. The 3D printer 114 produces a mechanically-accurate and spatially-accurate 3-D printed cardiovascular model 120, having the aforementioned mechanical and spatial accuracy of the patient's heart which was scanned during the MRI. The preferred embodiment uses elliptical data filling to deposit cellular materials onto the 3D printer hotbed plate; elliptical data filling is an insertion of data in a concentric-radial orientation, initializing the insertion at the center of a 3D printer hotbed plate, progressing toward the hotbed plate's perimeter. The above described process and system result in the capability to accurately reproduce a cardiovascular model of a patient's heart for use in pre-operative surgical training or other medical evaluation procedures. The cardiovascular-mechanical accuracy and the cardiovascular-spatial accuracy of the 3-D model, relative to the scanned organ (present on line 209), is bounded by the percentage-difference of mechanical and spatial properties resulting from the convolution of the nine-term, second order ranked tensor 116 with the K-Space dataset 145 of a feature space and a function space, performed by the MRI system 330. The accuracy, organ representation optimization, and time acquisition optimization of the cardiovascular model produced using the above described process results in an improvement of cardiovascular models currently produced by other methods and processes.

Figure 2:
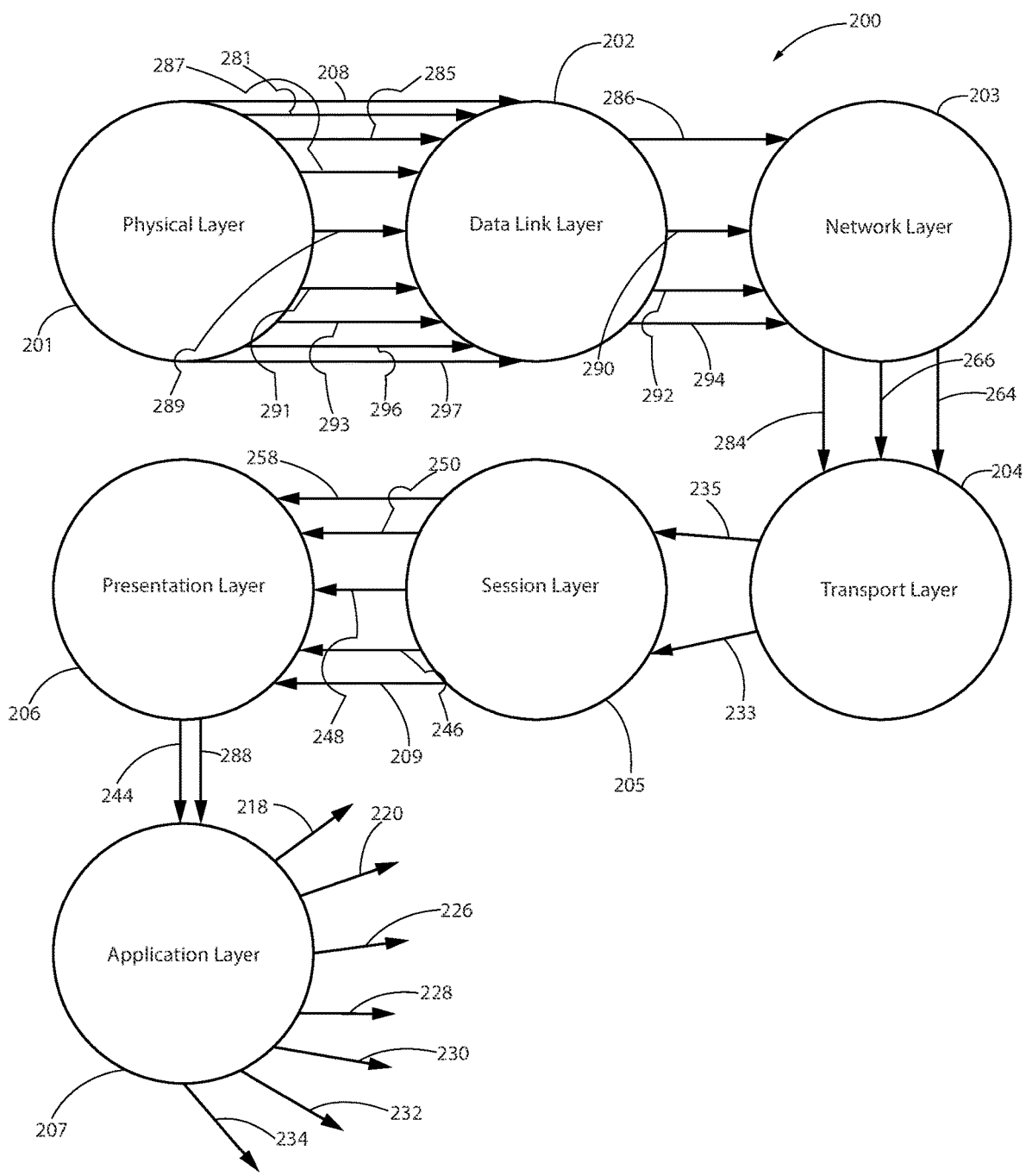
FIG. 2 is a drawing showing the network structure and element interconnections to implement the preferred embodiment of the invention.

The present invention may be configured to operate upon any number of network architecture designs. In the preferred embodiment a network connection is an inter-process communication path across a network 310 and between two processors such as a client and a server, over the internet or over similar systems of communication lines as depicted in FIG. 2. The type of network architecture intended for use includes commercial off the shelf physical devices such as switches, routers, buffers, wireless devices, and workstations. The type of software to operate the network architecture design requires operating systems and network protocols compatible with the hardware chosen. The preferred embodiment is implemented using the Open Systems Interconnect (OSI) reference model which describes a network architecture to allow data to pass between computer systems. The Physical Layer 201 defines the physical structure of the network and the topology. The Data Link Layer 202 provides error detection and correction. The Data Link Layer 202 uses two distinct sublayers which are Media Access Control and Logical Link Control layers to identify data type accessed. The Network Layer 203 handles the discovery of destination systems and addressing necessary to route data between network systems. The Transport Layer 204 provides connection services between the sending and receiving devices and ensures data reliability among network systems. The Session Layer 205 synchronizes the data exchange between applications initialized on separate devices. The Presentation Layer 206 translates data from the format used by the various applications into one that can be transmitted across the networked systems. The Application Layer 207 provides access to the network for the applications. The seven OSI layers (201, 202, 203, 204, 205, 206, and 207) depict the network architecture for the preferred embodiment of the present invention. The interconnecting arrow ended lines of the drawing 200 are control lines, bite stream lines, and may include other network devices such as switches and buffers one skilled in the art of network configuration and maintenance may deploy to implement the present invention.

Figure 3:
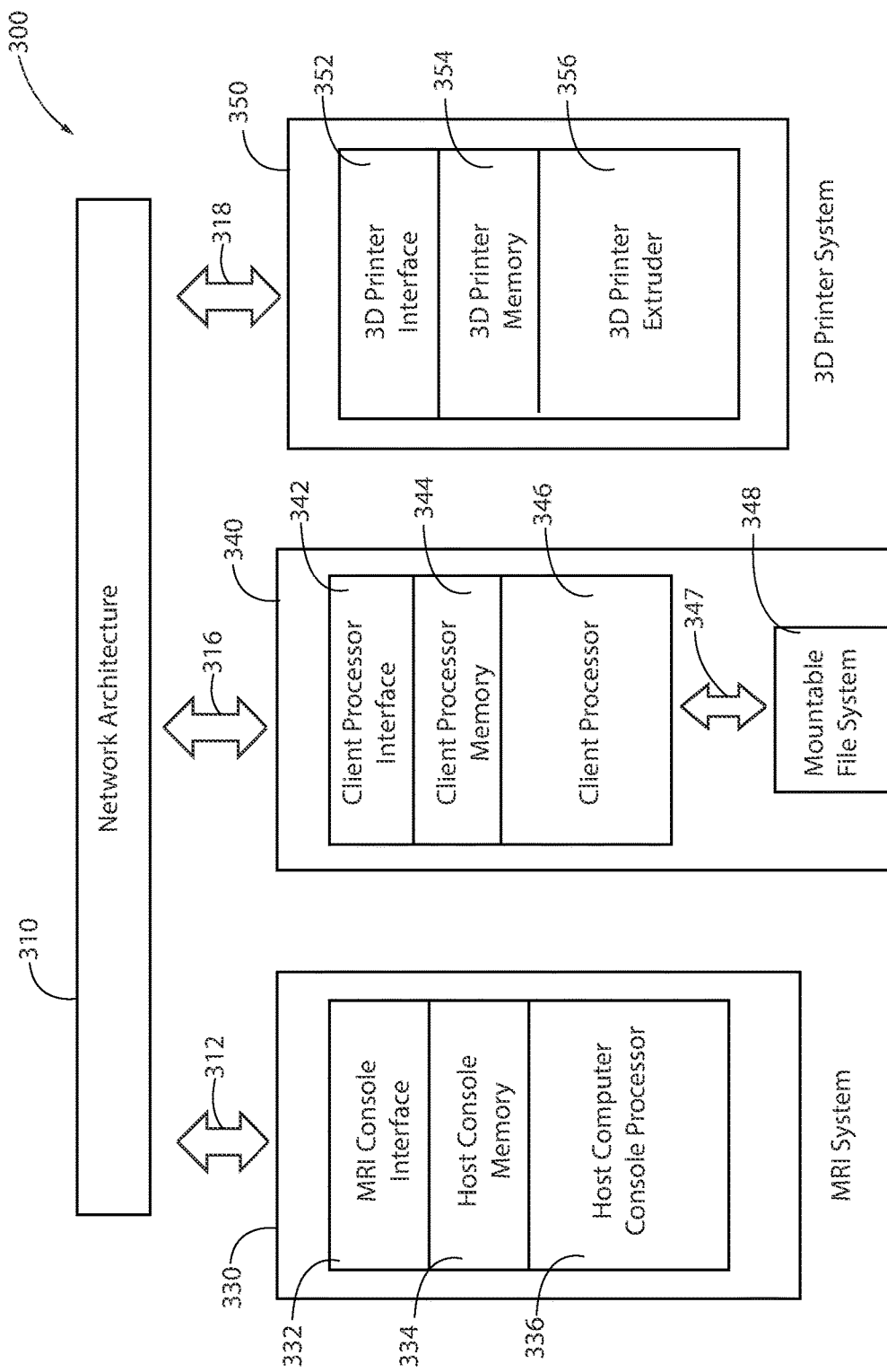
FIG. 3 depicts the functional configuration of the elements to practice the method and apparatus of the present invention and is not meant to be taken as a literal depiction of element arrangement.

The present invention is presented functionally in FIG. 3 300. The interplay between FIG. 2 200, network and control connectivity, and FIG. 3 300, functional operation of multiple computers and the network, is such that the combination of drawings allows one skilled in the arts of network configuration and administration and one skilled in the art of computer system engineering to practice the present invention.

The cardiovascular model 120 is 3-D printed which is configured to use a continuous medium, examples of such a continuous medium are 3-D printer filaments which are polymer-based filaments, or continuous metallic-based filaments, or continuous organic-materials-based filaments. In the preferred embodiment, the 3-D printer filament is thermoset plastic. An example of a 3-D printer which performs 3-D printer operations 114 using the additive manufacturing processes inherent to 3-D printing is a device based on Multi Jet Fusion technology which is a HP Jet Fusion 5420 W 3D Printer. There are other 3-D printer types such as fused deposition modeling, stereolithography, selective laser sintering, digital light processing, binder jetting, and directed energy deposit which may be selected to implement the present invention.

The cardiovascular mechanical properties and cardiovascular spatial properties are replicated in the completed organ model 120 by use of the continuous 3-D printer filament layers deposited by the 3-D printer extruder 356 according to 3-D printer operations 114.

The encoded cardiovascular mechanical properties and cardiovascular spatial properties are further processed (available on bite stream 258) by image and surface registration techniques 110, using a Gradient Estimation Volume Rendering application which initializes threading, where threading is the delegation of a computer process into discrete computer sub-processes, on client computer 346 parallel processing hardware, network communication line 287, where the preferred embodiment uses an NVIDIA GPU. The 3-D printer operations 114 utilize 3-D modeling software (line 220) as part of generating the driver file 113 (bite stream 220) examples of which are computer-aided design software, computer-aided manufacturing software, computer-aided engineering software, or printed circuit board design software, such as Autodesk Fusion 360, or RadiAnt DICOM Viewer. The 3-D modeling software is initialized, via network line 218, on the Client computer 340 in the preferred embodiment. The 3-D modeling software can also be described functionally as defining the additive layering of material to create complex structures having voids, channels, and density changes. The density of any particular section of the organ model 120 corresponds to the actual density of the biological material for the organ scanned during the MRI process. The 3-D printer interface 352 may be physically connected, or connected in a wireless fashion to the Client computer 340 via the network 232.

The Client computer 340 utilizes any number of computer processor technologies such as computer microprocessor technology, 64-bit computer architecture, any compatible operating system infrastructure, such as a Windows Enterprise Operating System, a Red Hat Enterprise Linux Operating System, or a VxWorks Operating System. The preferred embodiment uses 64-bit computer processing technology and the Red Hat Enterprise Linux Operating System. The Client computer 340 may be connected to the 3-D printer which executes 3-D printer operations 114 via a variety of network communication protocols, such as TCP/IP 233, UDP/IP 235, Serial Transmission, or Parallel Transmission. The preferred embodiment of the invention uses TCP/IP network communications protocol.

Turning to a description of the network connections 200 in conjunction with the functional description 300 of the present invention. It is recommended to the person practicing the invention, first assemble the hardware and software elements described below 300 and then build a physical network using the preferred embodiment of the network connectivity 200. A PCIe Passthrough 289, between the Client computer 340 and the MRI System 330, communicating on lines 248 and lines 250, results in the Client computer 340 mounting a mountable file system 348 which is used to copy the MRI k-space dataset 145 from the Host computer MRI System 330. The client computer 340 contains memory to load, execute, and store the processing results of the programs and applications it executes. In the preferred embodiment, a set of instructions for execution by a client computer processor 346 is a client program. The instructions are loaded into computer memory and are executed by the client processor. In the preferred embodiment a client processor 340 is a processing machine or processing device that accesses a shared resource on a server over a communications network 310. In the preferred embodiment, the databus lines (312, 316, 318) in the functional diagram 300 may include any number of buffers, bite stream lines, or data stream lines to practice the invention. The databus line 347 which provides large data transfers into the mountable file system 348 may be implemented as shown (bite stream 284), which is the preferred embodiment, or the mountable file system 348 may be connected directly to the network architecture 310 and hosted in its own server which is connected to the network architecture 310.

The computer program for the preferred embodiment contains instructions to implement the steps for the process 100 to produce an organ model 120. An organ model 120 is a representation, organized as a structural model hierarchy, of the elements to configure an anatomic and physiologic system of the MRI scanned organ. The term memory is used to identify an area of dynamic memory containing at least 128 gigabytes of storage. The client processor memory 344 is of several types: random access memory, cache memory, read only memory, and flash memory. The program code, program intermediate processing outputs, and the final processing outputs are stored and retrieved from the client processor memory 344. The PCIe Passthrough 289 may include the utilization of Kernel Virtual Machine Hypervisor technology, using bite stream 291 as, such as Xen hypervisor technology, or the utilization of computer-based Bootloader technology, Intel VT-d extension activation using bite stream 293, or AMD IOMMU extension activation using bite stream 297. The mountable file system 320 has random access memory also known as swap capable under the control of a C-programming language dynamic memory management. The MRI k-space dataset 145 is then transmitted from the Host computer console memory 334 to the Client computer 340, referring to bite stream 250. The hardware to transfer the MRI system k-space dataset 145 to the network architecture 310 includes a host computer console memory 334 having further included elements such as: registers a stack memory structure, a heap memory structure, a computer global memory space, SQL server, a not and (NAND) Flash memory storage, an High Density Digital (HDD) memory storage devices, or Solid State Drive (SDD) portable memory storage devices. The preferred embodiment uses HDD. The host computer console memory 334 is in communication with both the MRI Console interface 332 and the host computer console processor 336.

The utilization of computer network port scanning software, which is communicated on bite stream 228, is used as a means to identify a host computer Console interface 332 having a network port communicating on connection line 288. Port scanning is performed using network scanning software, such as Network Mapper (NMAP) software on the Client computer 340, mapping the TCP/IP-DICOM ports of the MRI Console interface 332.

The Host computer MR Console network TCP/IP-DICOM port is encoded with PCIe Bus lanes 285 between the Host computer PCIe Bus 208 and the Host computer Console interface 332 while the cardiovascular MRI exam is being performed. The MRI k-space dataset 145 of the cardiovascular MRI exam is transmitted across the PCIe Bus lanes 285 using transmission protocols of the PCIe Bus 208 which include, but are not limited to, Serial Transmission, Parallel Transmission communication protocols, Near Field Communication, radio frequency identification (RFID) technology, Smartcard technology, semiconductor technology, or any other computer network-connectivity methodology where any selection, or combination of an antenna transmitter, an antenna receiver, an antenna transceiver, memimductors, memcapacitors, or memresistors may be utilized in the process of data packet transmission or data packet reception between the host computer console processor 336, bite stream 250, and the Client computer processor interface 342, bit stream 248. Once the MRI console interface's network TCP/IP-DICOM ports are identified by the Client computer's 340 client processor interface 342, control lines 248, by computer network port scanning software, control lines 228, the client computer 340 sends a remote login or remote command line execution commands using control line 246. The remote login may be accomplished with Red Hat's Enterprise Linux secure shell (SSH) remote command networking command to the Host computer MRI Console interface 332, using control line 250, which uploads a C-programming language network data packet analyzer, control line 292. The data packet analyzer is a TCP/IP network data packet analyzer initialized on the Host computer MRI Console's PCIe Bus lanes 285. The Host computer MRI Console PCIe Bus 208 then transmits the MRI k-space dataset 145 (on connection 286) to the host computer MRI Console memory 334, data stream line 266. The C-programming language network data packet analyzer, bite stream 292, is assigned to the Host computer MRI Console network port interface 332 for which the Host computer MRI Console network port, line 281, is identified by initializing computer network port scanning software, line 228, by the Client computer 334, control line 248, onto the Host computer MRI Console interface 332, control line 250. The Client computer 340, bite stream 248, uploads a C-programming language data-log messaging service 296 to the Host computer MRI Console 334, bite stream 250. The C-programming language network data packet analyzer using control line 292, copies the MRI k-space dataset 145 bite stream 286, from the Host MR Console PCIe Bus lanes 285. The C-programming language network data packet analyzer on line 292 sets its configuration file in such a manner as to once the C-programming language network data packet analyzer on line 292 is prepared to transmit the collected MRI k-space dataset 145, the C-programming language network data packet analyzer on line 292 sends the collected MRI k-space dataset 145 to the mountable file system 348 on line 264. The mountable file system 348 once initialized by the Client computer 340, is visible to the MRI system 330, using bite stream 250. The C-programming language network data packet analyzer on line 292 sends its copied collection of the MRI k-space dataset 145 on data stream 286 to the C-programming language data-log messaging service on line 296. The C-programming language data-log messaging service 296 configures its copied MRI k-space dataset to be transmitted to the mountable file system 348, bite stream 264, of the Client computer 340. The C-programming language data-log messaging service, line 296, supports data communications endpoints for exchanging data between processes, such as Internet Protocol Sockets or Unix Domain Sockets, as a means for server network data transmissions, or server network data receptions, enabling local C-programming language data-log messaging services, or remote C-programming language data-log messaging services. The MRI k-space dataset on the mountable file system 348 of the Client computer 340 is swapped (network connection 290) into a Client computer data storage memory device 344, such as a NVMe M.2 SSD storage device, utilizing C-programming language dynamic memory management, which includes, but is not limited to, C-programming language pointers, C-programming language structures, or C-programming language functions such as malloc ( ), or free( ), as a means to allocate local computer resources. Local computer resources such as, but not limited to, internal memory buffers, random access memory (RAM), dynamic RAM (DRAM), static RAM (SRAM), or read only memory (ROM), on the Client computer's mountable file system 348 are expected for use. Logical volume management software (control line 294), such as the Red Hat Enterprise Linux Logical Volume Manager, performs dynamic memory management operations initialized by the Client computer 340 onto the MRI system 330, bite stream line 250, where the mountable file system 348 is stored, control line 264. The mountable file system 348, bite stream 264, is initialized by the Client computer 340, control line 248, mounting to the file system of the MRI Console interface, control line 250, is partitioned by the Client computer 340, control line 248, by utilization of physical computer storage device partitioning software, control line 244, such as Globally Unique Identifier Partitioning Tables, as a means to create the mountable file system 348, initialized by the Client computer processor 346, data stream line 248, onto the Host computer MR Console interface 332.

What is claimed is:

1. A method of producing a three dimensional model of a biological organ the method comprising:
   accepting a set of independent variables;
   accepting a set of dependent variables;
   accepting a set of scaling values;
   vector embedding a second order ranked tensor with information contained in the set of independent variables, contained in the set of dependent variables and contained in the set of scaling values resulting in an encoded second order ranked tensor;
   storing the encoded second ranked tensor on a client computer system;
   reading and unpacking a K-Space dataset content transferred from a host computer console computer system;
   superimposing the encoded second order ranked tensor onto the K-Space dataset content resulting in a superimposed dataset where the superimposed dataset processing is executed on the client computer system;
   time acquisition optimizing the superimposed dataset using a tensor decomposition software operation resulting in a tensor decomposition result where the tensor decomposition result processing is executed on the client computer system;
   simultaneously applying an image technique and a surface registration technique to the tensor decomposition result producing a volumetric dataset where the volumetric dataset processing is performed on the client computer system;
   performing a data type file conversion on the volumetric dataset producing a driver sequence file for controlling an additive layering printer where the driver sequence file processing is performed on the client computer system; and
   transferring the driver sequence file to a 3D printer system where the 3D printer system translates the driver sequence file into a set of instructions for controlling an additive layering printer filament type and an additive layering printer extruder motion to produce the three dimensional model where the three dimensional model represents the biological organ.

2. The method of claim 1, wherein the vector embedding further includes:
   establishing in first array the set of independent variables containing encoding information for cellular composition;
   establishing in a second array the set of dependent variables containing encoding information for elasticity, plasticity, and fracture;
   establishing in a third array the set of scalar values containing encoding information for a patient's age, race, and state of health; and
   combining the first array, the second array, the third array into an input array to encode the second order ranked tensor where the encoded second ranked tensor defines the deformation of continuous mediums as a plurality of voxel value parameterization for the three dimensional model of the biological organ when 3D printed.

3. The method of claim 1, wherein the time acquisition optimizing further comprises the steps of:
- evaluating the convolution dataset to determine a dimensionality reduction parameter where the dimensionality reduction parameter linearly corresponds to the convolution dataset size; and
- transforming an initial dimensional space of the convolution dataset to a lower dimensional space of a size reduced convolution dataset where the size reduced convolution dataset is reduced proportionally according to the dimensionality reduction parameter.

4. The method of claim 1 where the image technique and the surface registering technique further comprises the steps of:
- merging multiple data resources where the multiple data resources include image features for edges, corners, and blobs which conform structurally to the biological organ;
- supervising learning gradients where the learning gradients include information derived from the biological organ; and
- representing surfaces with transformation manifolds where the transformation manifolds eliminate sharp surface discontinuities in the three dimensional model of the biological organ.

5. The method of claim 1 where the volumetric dataset processing further comprises the steps of:
- projecting embedded data onto a feature space embodying anatomic components of the biological organ in the three dimensional model of the biological organ; and
- interpolating the embedded data to a function space embodying physiological components of the biological organ in the three dimensional model of the biological organ.

6. The method of claim 1 where the driver sequence file processing further comprises the steps of:
- accepting binary data conforming to anatomic and physiological structure of the biological organ;
- reading a set of binary instructions from a memory of the first client computer system;
- decoding the set of binary instructions read from the memory of the first client computer system; and
- executing the decoded set of binary instructions read from the memory of the client computer system to transform the binary data conforming to the anatomic and physiological structure of the biological organ to a plurality of voxel structures; and
- outputting a result of the executed set of decoded binary instructions to a client processor interface in communication with a 3D printer interface.

7. A non-transitory machine-readable storage device comprising instructions stored thereon, the instructions when executed by a computing processor causing:
- loading a computer port scanning set up file into a first computer memory of a client computer;
- execution of the port scanning set up file to initialize a plurality of communication ports connected to a network architecture;
- execution of a dynamic memory management controller of a client computer mountable file system to operatively configure the mountable file system where the dynamic memory management controller resides in a second computer memory of the client computer;
- collection of a K-space dataset produced by a magnetic resonance imaging device where the K-space dataset is stored in a first computer memory of a host console memory and the K-space dataset represents a scanned organ's physical characteristics;
- transferring the K-space dataset stored in the first computer memory of the host console memory to the client computer mountable file system;
- determination of a first set of values representing the scanned organ's structural properties;
- determination of a second set of values representing the scanned organ's cellular composition;
- determination of a third set of values representing a set of scaling factors related to a set of patient health quantifiable factors;
- execution of vector database instructions where the vector database instructions generates a plurality of second order ranked tensors then storing the plurality of second order ranked tensors into a second plurality of arrays written to the mountable file system;
- merging the first set of values, the second set of values, the third set of values with the K-space dataset into a first plurality of arrays where each array represents the scanned organ's physical characteristics contained within the K-space dataset;
- storing the first plurality of arrays in the mountable file system;
- execution of a time acquisition optimization process using the second plurality of arrays stored in the mountable file system and storing the result of the time optimization process in a third plurality of arrays stored in the mountable file system;
- loading an image and surface registration instruction set into a third computer memory of a client computer;
- executing the image and surface registration instruction set where the surface and registration instruction set processes the contents of the third plurality of arrays where the processes result is stored in a fourth plurality of arrays representing the scanned organ's structure where the fourth plurality of arrays is stored in the mountable file system;
- generation of a time optimized volumetric dataset representing the organ model's structural properties using the content of the fourth plurality of arrays as input;
- conversion of the time optimized volumetric dataset into a datatype file used to generate an additive printer driver file; and
- loading the additive printer driver file into an internal memory of an additive 3D printing device to construct a 3D organ model product containing the scanned organ's physical characteristics which includes a tissue variance, a cellular structure, and a physical structure.

8. The non-transitory machine-readable storage device of claim 7 further comprises instructions causing:
- buffering a first portion of the K-Space dataset in a first memory location in the mountable file system;
- storing a second portion of the K-Space dataset in a second memory location in the mountable file system;
- monitoring the available memory in the first memory location;
- monitoring the available memory in the second memory location;
- moving the first portion and the second portion of the K-space data out of the first memory location in the mountable file system to the second memory location when the first memory of the mountable file system is full; and
- storing the extracted K-space dataset into a first internal memory.

9. The non-transitory machine-readable storage device of claim 7 further includes instructions for:
- configuring a scalar portion of a vector database with the contents of a patient health history form;
- configuring a dependent variable portion of the vector database with mechanical information where the mechanical information is elasticity, plasticity, and fracture;
- configuring an independent variable portion of the vector database with cellular composition information; and
- combination of the scalar portion of a vector database, the dependent variable portion of the vector database, the independent portion of the vector database into an encoding array which defines the deformation of continuous mediums as a plurality of voxel value parameterization for the three dimensional model of the biological organ when 3D printed.

* * * * *